(12) United States Patent
Stoll (10) Patent No.: US 6,849,089 B2
(45) Date of Patent: Feb. 1, 2005

(54) IMPLANT WITH PROLIFERATION-INHIBITING SUBSTANCE

(75) Inventor: Hans-Peter Stoll, Wuerselen (DE)

(73) Assignee: Biotronik Mess-und Therapiegeraete GmbH & Co Ingenieurbuero Berlin, Berlin (DE)

( * ) Notice: Subject to any disclaimer, the term of this patent is extended or adjusted under 35 U.S.C. 154(b) by 94 days.

(21) Appl. No.: 10/263,393

(22) Filed: Oct. 2, 2002

(65) Prior Publication Data

US 2003/0069631 A1 Apr. 10, 2003

(30) Foreign Application Priority Data

Oct. 8, 2001 (DE) .......................................... 101 50 995

(51) Int. Cl.⁷ ................................................ A61F 2/06
(52) U.S. Cl. .................................................... 623/1.42
(58) Field of Search .............................. 623/1.38–1.46; 427/2.28, 2.24, 2.3

(56) References Cited

U.S. PATENT DOCUMENTS

| | | | |
|---|---|---|---|
| 5,843,172 A | 12/1998 | Yan | |
| 5,879,697 A | 3/1999 | Ding | |
| 5,968,092 A * | 10/1999 | Buscemi et al. | 128/898 |
| 5,980,551 A | 11/1999 | Summers | |
| 6,096,070 A | 8/2000 | Ragheb | |
| 6,153,252 A | 11/2000 | Hossainy | |
| 6,206,916 B1 | 3/2001 | Furst | |
| 6,284,305 B1 * | 9/2001 | Ding et al. | 427/2.28 |
| 6,355,055 B1 * | 3/2002 | Waksman et al. | 623/1.13 |
| 6,494,904 B1 * | 12/2002 | Love | 623/1.1 |
| 6,506,437 B1 * | 1/2003 | Harish et al. | 427/2.25 |
| 6,551,353 B1 * | 4/2003 | Baker et al. | 623/1.42 |
| 6,569,195 B2 * | 5/2003 | Yang et al. | 623/1.46 |
| 6,613,082 B2 * | 9/2003 | Yang | 623/1.42 |
| 6,613,084 B2 * | 9/2003 | Yang | 623/1.42 |
| 6,663,662 B2 * | 12/2003 | Pacetti et al. | 623/1.13 |
| 6,702,850 B1 * | 3/2004 | Byun et al. | 623/1.44 |
| 2002/0138100 A1 | 9/2002 | Stoll | |
| 2003/0139806 A1 * | 7/2003 | Haverkost et al. | 623/1.44 |
| 2004/0000046 A1 * | 1/2004 | Stinson | 29/426.4 |

FOREIGN PATENT DOCUMENTS

| | | | |
|---|---|---|---|
| CA | 2235031 | 4/1998 | |
| DE | 43 34 272 A1 | 4/1995 | |
| DE | 44 35 652 A1 | 4/1996 | |
| EP | 0 879 595 A1 | 11/1998 | |
| EP | 0 923 953 A2 | 6/1999 | |
| EP | 1 127 582 A2 | 8/2001 | |
| WO | WO 98/36784 A1 | 8/1998 | |
| WO | WO 00/12147 A1 | 3/2000 | |
| WO | WO 01/17577 A1 | 3/2001 | |
| WO | WO 01/41678 * | 6/2001 | 623/1.42 |
| WO | WO 01/54748 A1 | 8/2001 | |
| WO | WO 01/87376 A1 | 11/2001 | |

* cited by examiner

Primary Examiner—Suzette J. Jackson
(74) Attorney, Agent, or Firm—Hahn Loeser + Parks LLP (57) ABSTRACT

An implant for insertion in a portion of the human or animal blood circulation, in particular a stent, has a main body (2), at least a first material which is connected to the main body (2) and which includes at least one cell proliferation-inhibiting first substance, and a second material which decomposes in the implanted condition and which is of such an arrangement and nature that in a first condition prior to the commencement of its decomposition it prevents contact between the first substance and the surroundings of the main body (2) and in a second condition after the commencement of its decomposition it permits contact between the first substance and the surroundings of the main body (2) wherein the second material is further such that the second condition is achieved only after a first time interval which is sufficient for the formation of a body tissue coating (7) which encloses at least a portion of the surface of the main body (2).

20 Claims, 5 Drawing Sheets

IMPLANT WITH PROLIFERATION-INHIBITING SUBSTANCE

The present invention concerns an implant for insertion in a portion of the human or animal blood circulation, in particular a stent, comprising a main body, at least a first material which is connected to the main body and which includes at least one cell proliferation-inhibiting first substance, and a second material which decomposes in the implanted condition. The second material is of such an arrangement and nature that in a first condition prior to the commencement of its decomposition it prevents contact between the first substance and the surroundings of the main body and in a second condition after the commencement of its decomposition it permits contact between the first substance and the surroundings of the main body.

BACKGROUND OF THE ART

In the case of such intravascular or intracardial implants such as stents, electrode lines or the like, the problem which frequently arises is that uncontrolled cell growth is induced in the surrounding body tissue of the patient due to the foreign body which is not sufficiently biocompatible and which is represented by the implant, or due to injuries which occur in the implantation procedure in the adjoining body tissue.

That uncontrolled cell growth is undesirable. Thus for example in the case of intravascular implants it can have the result that the vessel passage is severely constricted by the proliferating tissue or is even completely closed in the short or long term. That is to be prevented in any case as such a vessel constriction or closure can under some circumstances bring about a life-threatening condition of the patient.

In order to counter that problem, for example, U.S. Pat. Nos. 6,153,252 and 6,206,916 B1 each disclose an implant of the general kind set forth, in the form of a stent, in which a cell proliferation-inhibiting substance is given off by a bioresorbable coating on the stent in order to suppress the uncontrolled cell growth of the vessel wall in the region of the stent. In order to delay the delivery of active substance or to cause it to take place more slowly, it is provided in that respect inter alia that a bioresorbable cover layer is disposed over the active substance-bearing coating.

The cell proliferation-inhibiting substances which are used in the known stents are generally operative in such a way that no cell growth worth mentioning occurs in the surroundings of the implant.

A further problem in connection with such intravascular or intracardial implants lies in their thrombogenic action, that is to say the increased risk of thrombosis that they entail. Depending on the respective degree of their biocompatibility, clots can comparatively easily be formed at the surface thereof. On the one hand they can also result in constriction or closure of the vessel portion in question, with the consequences which have already been referred to above. On the other hand such clots can also become detached from the location at which they are formed and transported with the bloodstream to remote, smaller blood vessels where they can then result in a so-called embolism, that is to say a constriction or blockage.

In order to obviate the problem of clot formation, it is provided in relation to known implants, in particular in relation to the above-mentioned stents, that one or more anti-thrombogenic substances are also to be liberated from a suitable coating in the manner referred to above.

In that respect however there is the problem that on the one hand the anti-thrombogenic substance is comparatively quickly transported away after it has been liberated, by virtue of the constantly occurring flow of blood, and therefore can achieve only a slight effect. The consequence of this is that a relatively large amount of the anti-thrombogenic substance has to be bound in the coating and liberated therefrom in order to achieve an effect which prevents the formation of clots.

On the other hand the constant flow of blood causes the active substance-carrying coating to be also relatively quickly washed out or cleared away so that the required long-term medication with an anti-thrombogenic effect cannot be achieved or can be achieved only at considerable cost, for example by means of a multiple coating with different levels of active substance concentration or delivery rates.

Therefore the object of the present invention is to provide an implant of the general kind set forth, which with simple means permits a long-term reduction in the risk of clot formation.

SUMMARY OF THE INVENTION

Based on an implant as set forth in the claims appended hereto, the present invention attains that object by the features also recited in the claims.

The present invention is based on the technical teaching that a simple and long-term reduction in the risk of thrombosis which is due to such an implant is achieved if firstly cell proliferation in the area around the implant is permitted until a body tissue coating which at least partially encloses the implant has been formed. That body tissue coating, by virtue of its being made up from the body's own cells, then forms a durable cover or layer which considerably reduces the risk of clotting, over the implant. It is only after that body tissue coating has been formed that a cell proliferation-inhibiting substance is caused to act in order to prevent uncontrolled cell growth which goes beyond the formation of the body tissue coating.

In accordance with the invention that is achieved in that the second material is such that the second condition in which the cell proliferation-inhibiting first substance takes effect as a consequence of decomposition of the second substance is achieved only after a first time interval which is sufficient for the formation of a body tissue coating which encloses at least a portion of the surface of the main body.

In that respect the body tissue coating preferably encases the remaining surface of the implant at least in the region in which the implant contacts the surrounding body tissue in the freshly implanted condition, that is to say immediately after implantation. It is particularly in that region that corresponding cell growth can occur, which permits the formation of the body tissue coating.

In the case of a stent, the portion which is to be enclosed is thus preferably the remaining surface of the stent in the region in which the external surface of the stent is in contact with the vessel wall. As a stent generally bears over its entire length against the vessel, the portion which is to be enclosed by the body tissue coating is usually the whole of the remaining surface of the stent, which surface does not directly contact the vessel wall.

The length of the first time interval is determined in accordance with the cell proliferation mechanisms which are operative at the respective location of implantation in the respective patient, in particular in accordance with the respective speed of cell growth. They may vary from one implantation location to another and from one patient to another, but can be readily ascertained in tests. The faster the cell growth at the location in question in the patient in question, the correspondingly shorter is the first time interval.

The patients can possibly be classified in different categories for which different lengths of the first interval are involved, in accordance with various factors that influence cell growth such as for example age, some other susceptibility but also other treatment or medication. If necessary it is even possible for the first interval to be matched to the individual patients on the basis of suitable investigations, that is to say a tailor-made implant can be made available for each respective patient.

The first time interval is preferably sufficient for the formation of a cover or casing of body tissue, which covers a portion of the surface of the main body. Particularly in the case of a stent which is implanted in a blood vessel, this involves preferably a cover of smooth muscle cells. Just a relatively thin layer of body tissue of that nature is fully sufficient for satisfying the aim to be achieved of covering the thrombogenic surface of the main body.

Depending on the respective implant involved it is preferably provided that the first interval is to be selected to be of such a length that the body tissue coating produced covers as far as possible the whole of the surface of the main body, around which blood flows, in order as far as possible to reduce the risk of clot formation at exposed regions of the surface of the main body.

As mentioned above the length of the first time interval depends on various factors. In order to ensure that a body tissue coating which is as continuous as possible and which covers the surface of the main body as comprehensively as possible is produced the first time interval is preferably a week. In order further to ensure that an excessively thick body tissue coating is not formed, it is further preferably provided that the first time interval is between two and four weeks.

The first material or at least one of the components thereof can be both biostable and also bioresorbable, that is to say in the implanted condition they break down because of the action of the body's own substances.

The first material may comprise a material which in itself has a suitably cell proliferation-inhibiting action. In other words the first material can exclusively consist of the first substance.

However the first material is preferably built up in the manner of a composite material as such a composite can be particularly well adapted to the many different demands made in respect of the chemical and physical and in particular the mechanical properties of the first material.

For that purpose the first material advantageously includes a first component which forms a matrix in which in turn the cell proliferation-inhibiting first substance is incorporated. In that respect in a simple case incorporation can finally be effected by purely mechanical bonding of the first substance in the matrix consisting of the first component. In other variants however this may equally also involve chemical bonding and a combination of chemical and mechanical bonding between the first substance and the first component.

The first substance can be so selected or can be of such a nature that it deploys its cell proliferation-inhibiting effect solely by corresponding contact without it having to be released for that purpose from its bonding within the first substance.

Particularly good results can be achieved however if the first substance is delivered in metered fashion to the surroundings, in suitably small amounts. That can be achieved for example if the first substance itself is bioresorbable or the composite as between the matrix and the first substance is broken up, for example by virtue of slow decomposition of the matrix.

The liberation rate and the progress thereof in respect of time, that is to say the liberation profile, of the first substance can be influenced within wide limits in known manner. Thus it can be provided for example that different amounts of the first substance are liberated at given times by virtue of a concentration gradient in respect of the first substance within the first material or by an arrangement of the first material in a plurality of layers with different concentrations of the first substance.

For example firstly a comparatively large amount of the first substance can be liberated per unit of time in order to inhibit cell proliferation as quickly as possible, by virtue of the decomposition of an outer layer with a relatively high level of concentration of the first substance. After a given time which is required for the substantially complete disintegration of that outer layer, which in other words therefore is governed by the thickness of the layer, the disintegration of a layer disposed therebeneath with a lower concentration of the first substance then begins. In that situation then only a smaller amount of the first substance is liberated per unit of time. That can be meaningful for example if the cell proliferation stimulus which is linked to the presence of the implant weakens after a certain time as a consequence of 'accustomisation' to the foreign body and the aim is to ensure that regeneration of the desired body tissue coating, which is necessary over time, is not also blocked by an excessively high dose.

A further possible way of influencing the liberation rate lies in the choice of the composition of the first component forming the matrix. Thus it can be provided that the nature of the matrix within the first material is varied, instead of the concentration of the first substance.

In order in that respect once again to adjust the liberation profile to the respective requirement involved, in a simple case it is possible to provide a plurality of layers whose matrix disintegrates at differing rates in order to achieve different liberation rates at given times. It will be appreciated however that the differing nature of the matrix can also be achieved by variations within an interconnected or continuous layer, for example by a variation in the thickness or the molecular weight and so forth of the matrix.

The variants just described above make it possible to achieve any liberation profiles which can be matched to the specific susceptibility and treatment of the patient, the implantation location and the desired treatment outcome. It will be appreciated that the variation in the concentration of the first substance and the variation in the nature of the matrix can naturally also be combined together in any manner.

It will be appreciated that, in advantageous variants of the implant according to the invention, it can also be provided that the first material contains a plurality of different cell proliferation-inhibiting first substances in order to achieve a cell proliferation-inhibiting action which is matched to the specific susceptibility and treatment of the patient, the implantation location and the desired treatment outcome.

A further possible way of influencing the configuration in respect of time of the cell proliferation-inhibiting action of the implant accordingly also involves using different first substances which have cell proliferation-inhibiting actions to varying degrees. They may then again be bonded similarly to the above-described variants in different successive layers in order to achieve cell proliferation inhibition of varying strengths, at different times.

The first material or at least a first of its components can be both biostable and also bioresorbable, that is to say it can disintegrate in the implanted condition by virtue of the action of the body's own materials.

The first material, as mentioned above, preferably includes at least a first component forming a matrix in which once again the first substance is incorporated. It will be appreciated however that it is also possible to provide a plurality of different components for the matrix. Suitably biocompatible polymers are preferably used for the matrix as the properties thereof can be particularly easily adjusted to the above-mentioned demands.

The second material is a bioresorbable material which can comprise one or more components which is or are the same as none of the components of the first material. The second material however may equally well be the same as a component of the first material. When the first material is made up from a matrix in which the first substance is incorporated the second material may for example comprise or correspond to the or one of the components of the first material, that forms the matrix.

Examples of suitable materials for the first material or its components, in particular for the cell proliferation-inhibiting first substance, as well as for the second material, have long been known so that there is no need to enter into a more detailed discussion in this respect at this juncture. A series of suitable materials can be found for example in the two above-cited U.S. Pat. (No. 6,153,252 and No. 6,206,916 B1), the disclosure of which is here expressly incorporated by reference thereto.

In advantageous variants of the implant according to the invention, there is provided at least one first deposit of the first material, which in the first condition is shielded by a covering of the second material, with respect to the surroundings of the main body. In that respect the covering does not necessarily have to shield the first material relative to the main body, it only has to ensure that there is no contact, or at least no contact worth mentioning, with the surroundings of the main body, in order to ensure that no cell proliferation-inhibiting action worth mentioning takes place prior to expiry of the first time interval.

The first deposit can be connected to the main body in any desired manner. In this respect there does not have to be a direct connection between the first deposit and the main body but the connection can also be indirectly by way of further intermediate elements.

The first deposit can be of many different kinds. In order to achieve a cell proliferation-inhibiting action which is distributed uniformly over the implant or at least over its regions which are relevant in the present context, the first deposit is either of a suitable extent or there is a series of first deposits which are suitably distributed over the implant.

Simple variants of the implant according to the invention provide that the first deposit is formed by a first layer which is connected to the main body while the covering is formed by a second layer which covers the first layer. In this case the first layer may cover the entire main body so that the first deposit extends over the entire implant. It may however also cover only a certain region of the surface of the main body. The aim in each case is only to ensure that, as indicated above, the second layer sufficiently well shields the first layer with respect to the surroundings.

In further preferred variants of the implant according to the invention the first deposit is arranged in a first opening or recess in the main body. The covering is then formed by a cover portion which closes or covers over at least the first recess. In that case the deposit can project partially above the surface of the main body, but it is preferably provided that the first deposit is arranged in sunk relationship in the main body. A comparable consideration applies to the cover portion. It can be arranged for example in such a way that its outer surface terminates flush with the surface of the main body, at least in the edge region of the first recess. Equally it can also be provided that the cover portion is formed by a continuous coating portion on the main body, which closes or covers a plurality of first deposits. Finally it will be appreciated that it can also be provided that the respective cover portion is formed by a punctiform coating portion on the main body.

The arrangement of the first deposit in the first recess can on the one hand provide for relatively simple anchoring of the first material. On the other hand, particularly advantageous arrangements can be achieved insofar as, depending on whether the deposit is entirely or partially sunk in the main body, the deposit is entirely or partially protected from transverse forces which otherwise could act on the deposit in opposition to the direction of movement of the implant when moving the implant to the implantation location.

If the first deposits are arranged in such first recesses, a further advantage is that, upon deformation of the main body as regularly occurs for example in the case of stents, there is a lesser risk of damage to the covering thereof by the second material. That is due to the fact that, by virtue of the discrete arrangement of the first deposits, in comparison with alternative configurations with first deposits comprising a continuous layer of larger surface area, in relation to the surface of the main body, a smaller proportion of the area is covered with pairings comprising the first and second materials. Overall therefore damage of the covering of the first material, for example tearing thereof, can occur only in the region of a smaller proportion of the surface area of the main body.

Further advantages along those lines are afforded if the respective recess is closed by a separate cover portion as, upon deformation of the main body, comparatively minor deformation effects then occur in the region of the pairing of cover portion and deposit, which deformation effects result in a comparatively low level of loading on the cover portion or the pairing of the cover portion and the deposit, whereby the risk of damage to the covering is further reduced.

The first recess can be produced in the main body in any suitable manner. It can already be formed directly in production of the main body. However it can also be produced by a suitable machining or processing step on a main body which has been previously manufactured. That can be effected for example by cutting or non-cutting machining of the main body. In that respect it is possible to use for example suitable etching processes or machining by means of lasers or the like. It will be noted that it is likewise possible for the first recess to be produced by a coating portion on a main body blank, the coating portion being suitably produced or arranged in suitably distributed manner.

The first recesses can be distributed uniformly over the implant by specifically targeted machining of the main body in order to achieve a cell proliferation-inhibiting action which is as uniform as possible over the whole of the relevant region of the implant. It will be noted that it is particularly easy to produce first deposits which are distributed uniformly over the main body when the main body has a porous surface at least in a portion-wise manner, for the purposes of forming a number of first recesses.

In other advantageous embodiments of the implant according to the invention it is provided that the first deposit is enclosed in a microcapsule of the second material, which microcapsule forms the covering and is connected to the main body. That variant affords the advantage that the risk of damage to the covering of the first material is greatly reduced by the second material in the event of deformation of the main body. The microcapsule can readily follow the deformation of the main body without the situation involving the wall of the microcapsule being heavily loaded.

In general a relatively large number of such microcapsules is distributed over the implant or the region of the implant which is crucial here. Then those microcapsules each contain only a comparatively small amount of the first material. Even if individual microcapsules should then be damaged upon deformation of the implant, this does not involve any cell proliferation-inhibiting effect worth mentioning, as at best only the comparatively small amount of the first substance, which is contained in the microcapsules in question, can deploy its action.

The microcapsules can be arranged in one or more layers on the surface of the main body. In the event of suitably dense packing of the microcapsules in a plurality of layers slow liberation of the first substance can be achieved over a certain period of time as at least preferably initially the more outwardly disposed microcapsules disintegrate and subsequently the first substance contained therein is liberated.

In other variants, metered liberation of the first substance can be effected by the microcapsules being of differing wall thicknesses, that is to say liberation of the first substance can begin only after a given delay, depending on the respective wall thickness involved. The same effect can be achieved if differing materials which decompose at differing speeds are used for the microcapsules.

The microcapsules in turn can also be arranged or accumulated in suitable first recesses in the main body. That arrangement combines the advantages of the microcapsules with the above-discussed advantages of arranging the first deposit in first recesses of that kind. In particular the microcapsules in those recesses are protected from the action of external forces and thus damage thereto or removal from the implant.

The bonding of the microcapsules to the main body and possibly the connection thereof to each other can be effected in any known manner. Thus for example the microcapsules can be connected to each other and/or to the main body by a suitable adhesive or the like. Equally it will be appreciated that it can be provided that the microcapsules are connected to each other and/or to the main body by a sintering-like process by partial fusion of their surfaces to each other.

It will be appreciated that the variants described above in respect of the arrangement and configuration of the first deposit can also be combined together in any desired manner. Thus microcapsules can be provided for example in mechanically heavily loaded regions while deposits of larger area or larger volume, of the kinds described hereinbefore, are provided in less heavily loaded regions.

Further preferred configurations of the implant according to the invention are distinguished in that, to promote cell proliferation prior to expiry of the first time interval, there is provided a third material which is connected to the main body and which includes a cell proliferation-promoting second substance. That can provide that the first body tissue coating which reduces the risk of clotting is formed as quickly and as targetedly as possible. It will be appreciated that in these variants the first time interval can be correspondingly shorter, by virtue of the acceleration achieved in forming the first body tissue coating.

The third material can be arranged in at least one second deposit. That second deposit can be arranged and formed in the same manner as the above-described first deposit. In that respect it can also be provided that the second deposit is provided with a corresponding shielding by means of a further, fourth material which causes the cell proliferation-promoting action to start, with a delay by a second time interval. It will be appreciated in that respect that the fourth material can correspond to the second material. It will further be appreciated that the second time interval is correspondingly shorter than the first time interval.

Preferably there is once again a number of second deposits which are preferably suitably uniformly distributed over the main body or the decisive region of the main body in order to achieve a cell proliferation-promoting action which is as uniform as possible and thus a first body tissue coating which is as uniform as possible.

Moreover it can also be provided that it is not a separate third material but the second material which forms the shielding for the first material that corresponds to the third material, accordingly therefore the second material includes the cell proliferation-promoting second substance. As soon as that second material including the cell proliferation-promoting second substance is then disintegrated and thus the first material is exposed, the action of the cell proliferation-inhibiting first substance then begins.

The cell proliferation-promoting and the cell proliferation-inhibiting actions can overlap each other, that is to say the action of the second substance can still persist when the action of the first substance is already beginning. In preferred embodiments of the implant according to the invention the third material is such, in particular the concentration of the second substance is so selected, that the cell proliferation-promoting action is substantially concluded prior to or with the expiry of the first time interval.

It will be appreciated that, in further variants of the invention, by means of a suitable configuration and/or arrangement of first and second deposits, it is also possible to provide that phases in which a cell proliferation-inhibiting or a cell proliferation-promoting action is achieved by the liberation of corresponding first or second substances respectively trigger each other in respect of time.

The invention can be applied to any intravascular or intracardial implant types, such as for example electrodes and so forth. It can be transposed to particular advantage however if the implant is a stent, in particular a coronary stent.

It will be appreciated that the described first, second and third materials can be applied to the implant in any known manner by suitable coating processes or the like. In particular it is possible for one or more of those materials to be applied to the implant for example by the treating surgeon, immediately prior to the operation, by a dip process which is frequently also referred to as 'dip coating'.

BRIEF DESCRIPTION OF THE DRAWINGS

Further advantageous configurations of the invention are set forth in the appendant claims and the description hereinafter of preferred embodiments, which refers to the accompanying drawings in which:

DETAILED DESCRIPTION OF THE DRAWINGS

Figure 1:
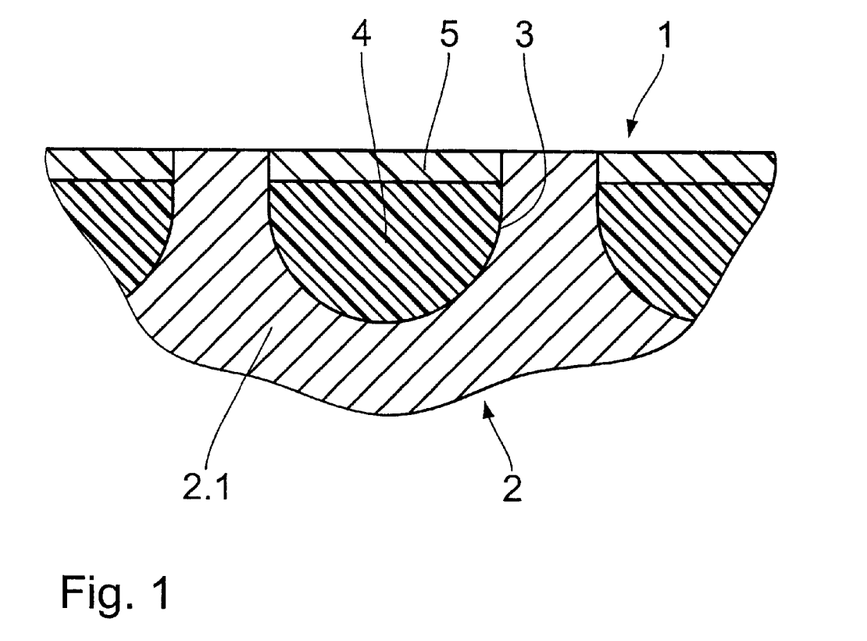
FIG. 1 is a diagrammatic view in section through part of a preferred embodiment of the implant according to the invention.

FIG. 1 shows a diagrammatic view in section through part of a preferred embodiment of an implant according to the invention in the form of a stent 1 having a main body 2. The main body 2 is of a tubular configuration, wherein the peripheral portion thereof is apertured in a mesh-like manner and comprises land or bar elements 2.1 which define the openings in the peripheral portion of the main body 2.

The bar element 2.1 shown in FIG. 1 has a number of first recesses 3. A first deposit 4 comprising a first material is arranged in each of those first recesses 3. The first deposit 4 is shielded with respect to the surroundings of the main body 2 by a covering in the form of a cover portion 5 in a first condition prior to or immediately after implantation.

The deposits 4 are distributed uniformly over the entire main body 2 of the stent 1. In this respect they are disposed both on the portion of the surface of the main body 2, which faces towards the wall of a blood vessel, and also on the portion of the surface of the main body 2, which faces towards the lumen of the blood vessel in question.

It will be appreciated however that in other embodiments it can be provided on the one hand that the first deposits are distributed more or less uniformly over the entire surface of the stent. Likewise it is possible for the surface portions to be provided with corresponding first deposits which directly delimit the openings in the peripheral portion of the main body. Finally it will be appreciated that it is also possible for said surface portions to be provided alone or in any combinations with corresponding first deposits.

The first recesses 3 are specifically targetedly formed in the main body 2 by suitable machining, for example by means of a laser. They are of a defined geometry. It will be appreciated however that, in other variants of the implant according to the invention, the first recesses can also be formed for example by a suitably porous surface region of the main body. The first deposits can then be arranged in the pores of the main body.

The first deposit 4 and the cover portion 5 are sunk into the bar element 2.1 of the main body 2 in such a way that the outside surface of the cover portion 5 terminates flush with the surface of the main body 2. That ensures that, when the stent 1 is being moved to the implantation location, no transverse forces act on the first deposit 4 or the cover portion 5, which could adversely affect the respective anchoring thereof to the main body 2.

A further advantage of the configuration with a separate cover portion 5 for each first deposit 4 is that the risk of damage to the covering of the first deposit 4 by the covering portion 5 is reduced, which risk arises as a consequence of deformation of the stent when it is being moved to the implantation location and in particular upon expansion of the stent. That is due to the fact that the bar elements 2.1 are subjected to only relatively slight deformation effects in the region of each individual first deposit 4, thereby also locally involving only relatively low levels of loading on the cover portion 5 and the first deposit 4 respectively.

The first material comprises a matrix of a bioresorbable polymer, that is to say a polymer which decomposes under the action of materials in the actual body of the patient. Particles of a first substance which has a cell proliferation-inhibiting action are incorporated in the matrix of the first material. The second material comprises an also bioresorbable polymer which however does not have a cell proliferation-inhibiting action and in particular no corresponding incorporations.

The configuration and in particular the thickness of the cover portion 5 is so selected in dependence on the properties of the second material that, as a consequence of decomposition of the cover portion 5, in a second condition, contact occurs between the first substance and the body tissue adjoining the stent 1 or body fluids flowing around the stent 1 at that location, only after the expiry of a first time interval after implantation of the stent 1.

Figure 2A:
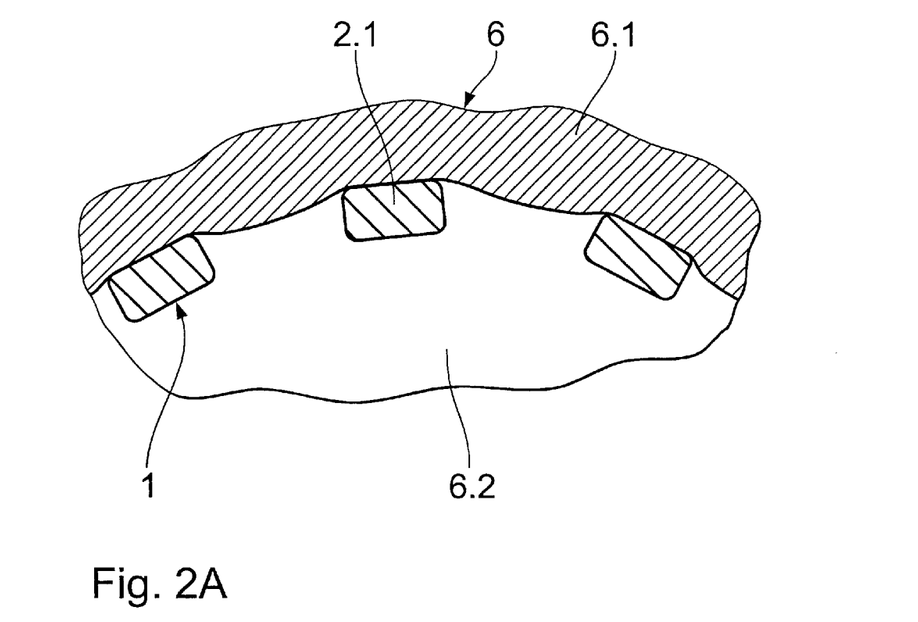
FIGS. 2A and 2B are further diagrammatic views in section through part of the implant of FIG. 1 when inserted into the body, at different moments in time.
Figure 2B:
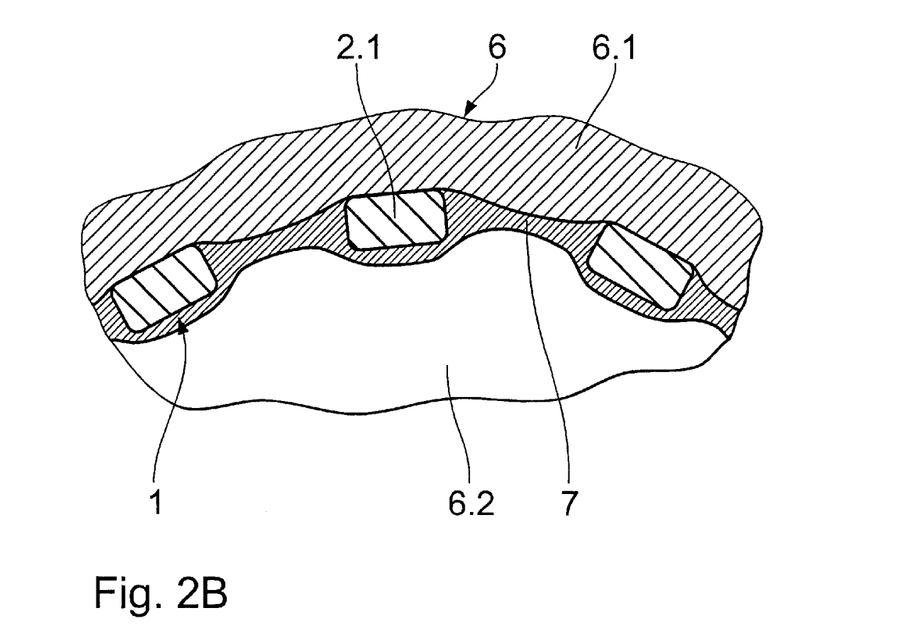

FIGS. 2A and 2B show the stent 1 in the first and second conditions. In that respect FIG. 2A represents the first condition at the moment in time immediately after expansion of the stent 1 at the location of implantation in the blood vessel 6. The bar elements 2.1 of the main body 2 contact the wall 6.1 of the blood vessel 6 over the entire length of the main body and hold the blood vessel wall expanded in order to permit a normal flow of blood through the lumen 6.2 of the blood vessel 6.

The first time interval is so selected that, after the expiry thereof, that is to say upon the occurrence of the second condition, a body tissue coating 7 has been formed, which encloses the portions of the surface of the bar elements 2.1, which are not in contact with the wall 6.1 of the blood vessel 6, as is shown in FIG. 2B. The cover 7 substantially comprises smooth muscle cells which occur primarily as a consequence of cell proliferation mechanisms in respect of the tunica intima and media of the blood vessel 6. In this respect the cell proliferation mechanisms are induced primarily by the presence of the foreign body which the stent 1 represents.

In the present case the first time interval is about two weeks. It will be appreciated however that different first time intervals can also be selected depending on the respective disposition of the patient, the patient's medication and the implantation location.

As soon as the cell proliferation-inhibiting first substance is liberated by virtue of disintegration of the polymer matrix of the first material of the first deposit 4, that suppresses further growth of the cover 7 to an extent which ensures that there is no partial or indeed complete obstruction of the lumen 6.2 due to uncontrolled cell growth.

It is provided in the present case that the same concentration of the first substance obtains over the entire deposit 4, in other words therefore the first substance is distributed uniformly over the entire deposit 4. Accordingly, in relation to time, there is initially approximately a constant liberation rate for the first substance. The arcuate sectional contour in the bottom of the recesses 3 however means that the surface area of the deposit, which is operative upon decomposition of the polymer matrix, becomes progressively smaller at an advancing moment in time so that the liberation rate of the first substance continuously decreases from a given moment in time.

The polymer matrix of the first substance decomposes only very slowly so that the cell proliferation-inhibiting effect persists over a sufficiently long period of time. The slow decay in the cell proliferation-inhibiting effect can be tolerated in that respect as with time the body becomes accustomed to the foreign body in the form of the stent 1.

By virtue of being made up from the body's own cells the cover 7 forms so-to-speak a natural coating on the stent 1, which markedly reduces the risk of clotting in comparison with an exposed stent. It is thus possible to forego anti-thrombogenic medication of the patient, for example by liberating an anti-thombogenic substance from suitable deposits on the stent or by systemic medication.

Figure 3:
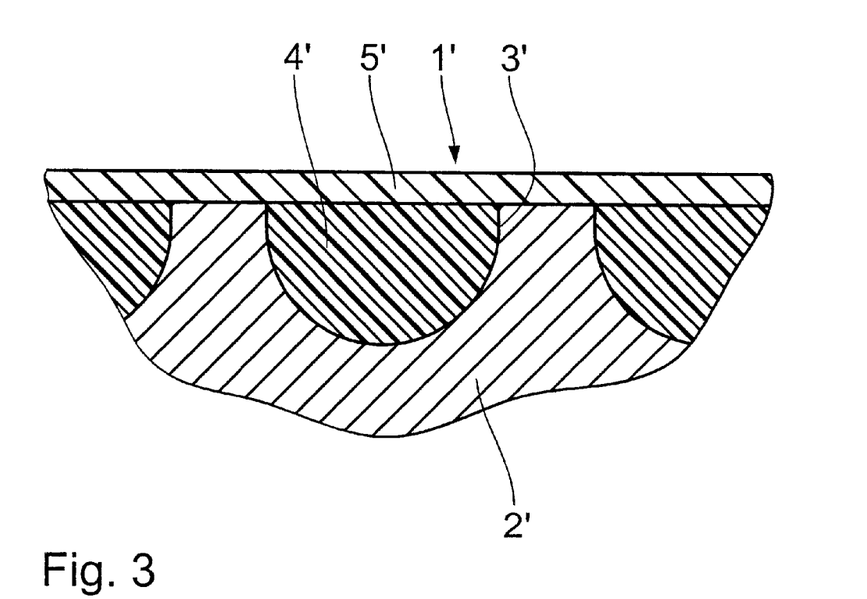
FIG. 3 is a diagrammatic view in section through part of a further preferred embodiment of the implant according to the invention.

FIG. 3 is a diagrammatic view in section through part of a further preferred embodiment of a stent 1' according to the invention, which substantially corresponds to the embodiment of FIG. 1, so that only the differences will be discussed here.

The difference is that the first deposits 4' which are recessed in the first recesses 3' in the main body 2' are not each closed off by a separate cover portion but a plurality of first deposits 4' are shielded with respect to the surroundings of the main body 2' by a common covering in the form of a layer 5' on the surface of the main body 2'.

In this respect the layer 5' again comprises the same second material as was already used for the covers in the variant in FIG. 1. Likewise the first deposits 4' comprise the same first material as was described hereinbefore with reference to FIG. 1.

Figure 4:
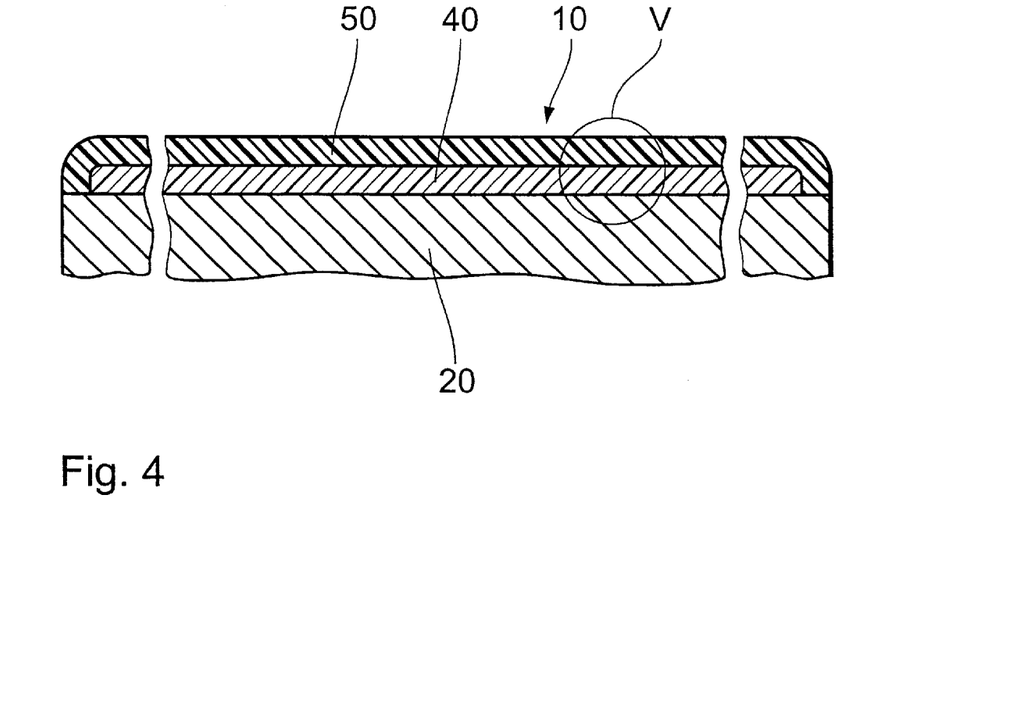
FIG. 4 is a diagrammatic view in section through part of another preferred embodiment of the implant according to the invention.

FIG. 4 shows a diagrammatic view in section through a further preferred variant of an implant 10 according to the invention. It has a main body 20 on the surface of which is arranged a first deposit in the form of a first layer 40 of a first material. That first layer 40 is shielded from the surroundings of the main body 20 by a shielding in the form of a second layer 50 which is disposed over the first layer 40.

The second layer 50 again comprises a bioresorbable polymer which decomposes so slowly that the first condition in which contact is possible between the first layer 40 and the surroundings of the main body 20 by virtue of decomposition of the second layer 50 occurs only after the expiry of a first time interval of three weeks.

In the illustrated example the first material of the first layer 40 again comprises a matrix of a bioresorbable polymer to which molecules of a cell proliferation-inhibiting first substance are bound. The polymer matrix disintegrates under the action of the body's own substances, in which case then also the bonding of the molecules of the first substance to the matrix polymer is broken up and the cell proliferation-inhibiting action thereof begins. Decomposition takes place correspondingly slowly so that the cell proliferation-inhibiting action due to liberation of the first substance is maintained over a sufficiently long period of time.

It will be appreciated that in other variants of the invention the first layer may also comprise a first material which in itself has a cell proliferation-inhibiting action and which thus so-to-speak itself represents the first substance in the sense of the present invention.

It will further be appreciated that in other variants it can also be provided that the first substance for the first layer can also involve a biostable material which deploys its cell proliferation-inhibiting action solely by virtue of contact with the surroundings of the main body.

The implant in FIG. 4 involves an electrode which can be anchored in the wall of a vessel or a wall of the heart. In this case the first and second layers 40 and 50 are arranged at least in that region of the electrode 10, which involves direct contact with the body tissue, so that there the protective body tissue coating can be formed over the electrode surface.

In FIG. 4 only a portion of the surface of the main body 20 is provided with a first layer 40 and a second layer 50 for shielding same. It will be appreciated that in other variants a plurality of surface portions but also the entire surface may be provided with corresponding first and second layers.

Figure 5:
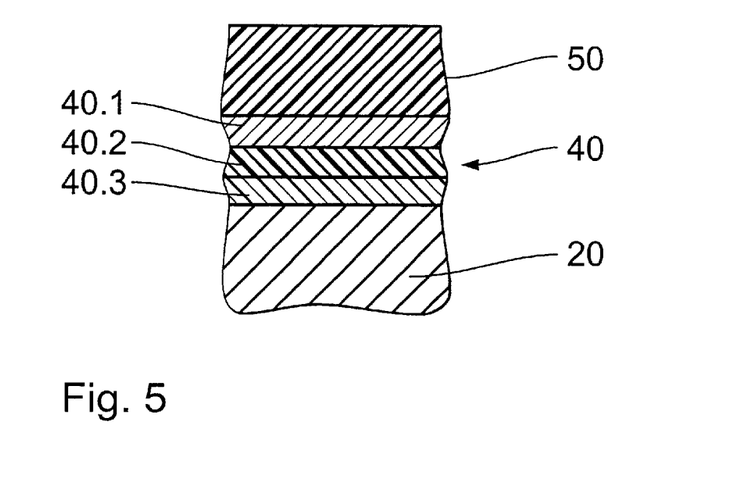
FIG. 5 shows the detail V in FIG. 4.

FIG. 5 shows the detail V from FIG. 4. As can be seen from FIG. 5 the first layer 40 comprises three different sub-layers 40.1, 40.2 and 40.3 which each comprise the first material. The difference is that the first substance in each respective sub-layer is present in a differing level of concentration. Thus the concentration of the first substance decreases stepwise from the first sub-layer 40.1 by way of the second sub-layer 40.2 to the third sub-layer 40.3. Accordingly in this case also there is initially a comparatively strong cell proliferation-inhibiting action which then decreases stepwise at the transition in each case to the next sub-layer.

It will be appreciated that in other variants it can be provided that such a concentration gradient in respect of the first substance is achieved, possibly also steplessly, in a single layer. It will likewise be appreciated that the concentration of the first substance can also vary in any other manner, over the first layer.

Figure 6:
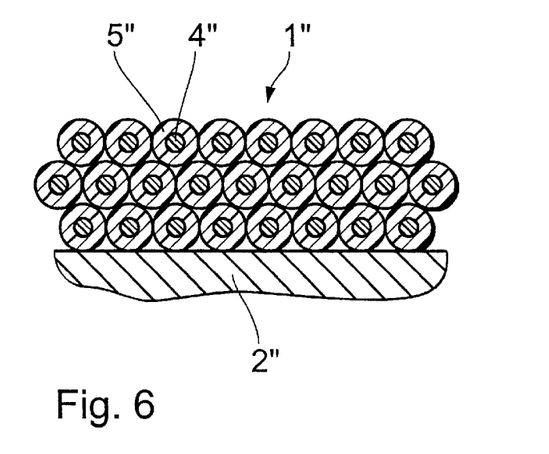
FIG. 6 shows a diagrammatic view in section through part of a further preferred embodiment of the implant according to the invention.

FIG. 6 shows a further variant of the stent 1" according to the invention with a main body 2", on the surface of which microcapsules 5" are arranged in a plurality of irregular layers. In this case the main body 2" except for the first recesses corresponds to the main body shown in FIG. 1 so that this does not need to be considered in greater detail here.

A respective first deposit 4" of a first material is enclosed in each of the microcapsules 5". The wall of the microcapsules 5" thus forms as it were a shielding for the first material, relative to the surroundings of the main body 2".

The first deposit 2" comprises a first material which in itself has a cell proliferation-inhibiting action and which thus so-to-speak itself represents the first substance in the sense of the present invention.

It will again be appreciated that, in further variants of the invention, the first material, as was also described hereinbefore with reference to other embodiments, can comprise a matrix of a bioresorbable polymer in which particles of a cell proliferation-inhibiting first substance are incorporated. The polymer matrix then again breaks down suitably slowly under the action of the body's own substances so that the cell proliferation-inhibiting action by virtue of liberation of the first substance is maintained over a sufficiently long period of time.

The wall of the microcapsules 5" again comprises a bioresorbable polymer which decomposes so slowly that the second condition in which contact is possible between the first deposit 4" and the surroundings of the main body 2" by virtue of decomposition of the microcapsules 5" in question occurs only after the expiry of a first time interval of four weeks.

The microcapsules 5" are connected to the surface of the main body 2" and to each other by a suitable adhesive. The adhesive and the second material have sufficient toughness to be able to follow deformations of the main body and thus to prevent unwanted detachment of the microcapsules 5" from the stent 1".

Fitting the microcapsules 5" in a plurality of layers ensures that the first substance is liberated over a longer period of time. That is due to the fact that correspondingly dense packing of the microcapsules 5" means that initially only the upper layer of the microcapsules 5" is decomposed by the action of the body's own substances while the lower layers initially remain substantially unaffected. Decomposition then advances only relatively slowly to the lowermost layer.

Figure 7:
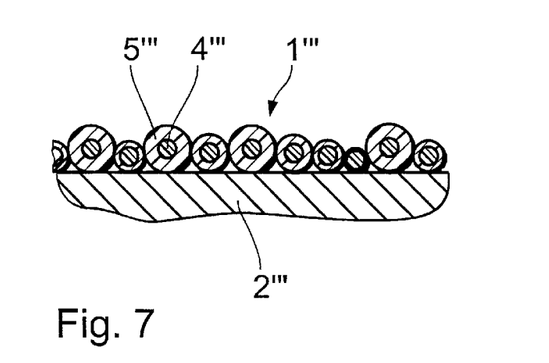
FIG. 7 shows a diagrammatic view in section through part of a further preferred embodiment of the implant according to the invention.

FIG. 7 shows a further preferred variant of a stent 1'" according to the invention which in terms of its basic structure does not differ from that shown in FIG. 6 so that here only the differences will be discussed in greater detail.

The difference is that the microcapsules 5'" with the first deposits 4'" are arranged in only one layer on the main body 2'", but in that respect they are of different wall thicknesses. That ensures that the first substance is delivered after expiry of the first time interval, over a longer period of time.

In this case the microcapsules 5'" with the smallest wall thickness define the first time interval. The liberation rates at given times can be easily controlled for example by way of the respective proportion of the microcapsules 5'" of a given wall thickness in relation to the total amount of the microcapsules 5'".

It will be appreciated that a comparable effect can be achieved with other variants of the invention in that, with all microcapsules being of the same wall thickness, different second materials are used, which decompose at various rates.

Figure 8:
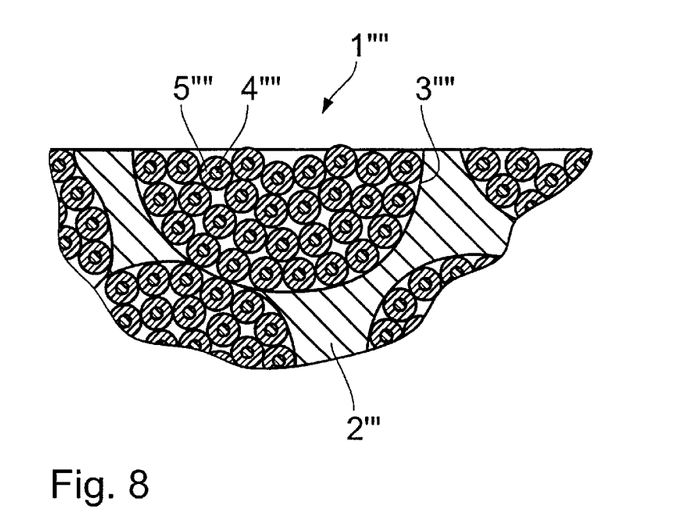
FIG. 8 shows a diagrammatic view in section through part of a further preferred embodiment of the implant according to the invention and FIG. 9 shows a diagrammatic view in section through part of a further preferred embodiment of the implant according to the invention.

FIG. 8 shows another preferred variant of a stent 1"" according to the invention which in terms of its basic structure does not differ from that shown in FIG. 6 so that in this case also only the differences are to be discussed.

The difference is that the main body 2"" has an open-pore surface and the microcapsules 5"" with the first deposit 4"" are incorporated in the first recesses formed by the pores 3"". That provides that the microcapsules 5"" are protected from the action of external forces upon being moved to the implantation location and thus from premature mechanical removal which would result therefrom.

The variants with microcapsules, shown in FIGS. 6 through 8, involve a particularly low level of risk of premature liberation of the cell proliferation-inhibiting first substance as a consequence of damage to the shielding by virtue of the second material. That is due to the fact that, even in the event of comparatively severe deformation of the main body, the individual shielding means, that is to say the walls of the microcapsules, can well follow such deformation as a result of their toughness and possibly the toughness of their connection and accordingly are also subjected to only relatively low loadings.

The risk of damage to the shielding can also be further reduced inter alia if the connection, for example the adhesive used for that purpose, is of a somewhat lower level of strength than the wall of the microcapsules. Failure then occurs in the event of severe deformation only at the connecting locations so that the microcapsules themselves remain intact.

Figure 9:
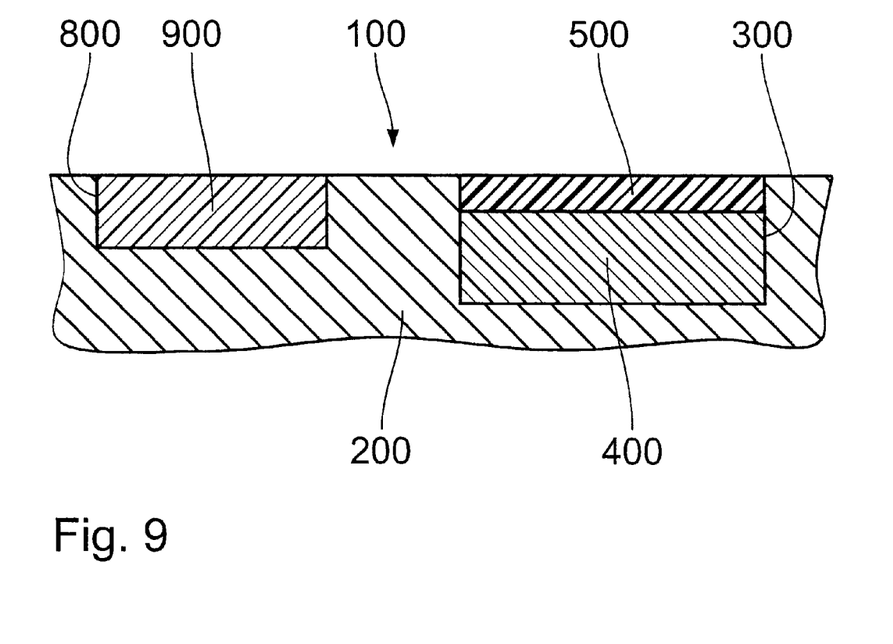

Finally FIG. 9 shows a further advantageous configuration of an implant 100 according to the invention which has a main body 200. Arranged in the main body 200 is a first recess 300 in which a first deposit 400 is let. The first deposit 400 is shielded relative to the surroundings of the main body 200 by a cover portion 500.

The first deposit 400 comprises a bioresorbable first material which contains a cell proliferation-inhibiting first substance. The cover portion 500 comprises a bioresorbable second material. The first deposit 400 and the cover portion 500 correspond in their structure and function to the first deposit 400 and the cover portion 5 shown in FIG. 1 so that this will not be discussed in greater detail, but reference will be made to the foregoing description relating to FIG. 1.

Also provided in the main body 200 is a second recess 800 in which a second deposit 900 is arranged. That second deposit comprises a third material which contains a cell proliferation-promoting second substance which is incorporated in a matrix of a bioresorbable polymer.

A series of first deposits 400 and second deposits 900 are distributed uniformly over the main body 200 so that the corresponding actions occur distributed uniformly over the implant 100.

Liberation of the second substance is effected by virtue of decomposition of the polymer matrix of the third material, which starts straightaway, immediately after implantation of the implant 100. That accelerates the formation of a body tissue coating which encloses exposed surface portions of the implant, as was described hereinbefore with reference to FIGS. 2A and 2B.

The second deposit 900 and in particular the polymer matrix of the third material is such that decomposition and thus liberation of the cell proliferation-promoting second substance terminates prior to expiry of the first time interval, that is to say prior to the commencement of liberation of the cell proliferation-inhibiting first substance from the first deposit 400.

The first time interval is shorter than in the above-described variants, by virtue of the corresponding configuration of the cover portion 500, in particular by virtue of a suitable choice of the second material used for same, as a consequence of the accelerated formation of the enclosing body tissue coating. It is approximately one week.

In alternative embodiments a comparable effect can be achieved if in a configuration as is shown in relation to one of the above-described Figures, the second material includes a suitably cell proliferation-promoting second substance.

Although the implant according to the invention was described hereinbefore almost exclusively in relation to stents, it will be appreciated that the invention can also be applied to any other intravascular or intracardial implants types such as for example electrodes and so forth.

What is claimed is:

1. An implant for insertion into a portion of a circulatory system of a human or an animal, comprising:

a main body having a surface and a surrounding area;

at least one first material connected to the main body and including at least one cell proliferation-inhibiting first substance;

a second material which decomposes in an implanted condition and which prevents contact between the first substance and the surrounding area of the main body while in a first condition before beginning to decompose and which permits contact between the first substance and the surrounding area of the main body while in a second condition after beginning to decompose; and a third material which is connected to the main body and which includes a cell proliferation-promoting second substance;

wherein the second material achieves the second condition only after a first time interval which is sufficient for a body tissue coating to form and enclose at least a portion of the main body surface, and the first time interval is at least a week, and wherein the first material is present with respect to the surrounding area of the main body in a first deposit, which in the first condition is shielded by a covering of the second material, and wherein the third material promotes cell proliferation prior to expiry of the first time interval.

2. The implant of claim 1, wherein:
the first deposit is formed by a first layer connected to the main body and the covering is formed by a second layer covering the first layer.

3. The implant of claim 1, wherein:
the first deposit is arranged in a first recess of the main body, the covering being formed by a cover portion closing the first recess.

4. The implant of claim 3, wherein:
at least a portion of the main body surface is porous for forming a number of first recesses.

5. The implant of claim 1, wherein:
the first deposit is enclosed in a microcapsule which forms the covering and which is connected to the main body.

6. The implant of claim 1, wherein:
the concentration and nature of the second substance are so selected that the cell proliferation-promoting action is substantially concluded prior to or with the expiry of the first time interval.

7. The implant of claim 1, wherein:
the main body comprises a stent.

8. The implant of claim 1, wherein:
the first time interval is at least two weeks.

9. The implant of claim 8, wherein:
the first time interval is less than four weeks.

10. The implant of claim 1, wherein:
the main body comprises a stent.

11. An implant for insertion into a portion of a circulatory system of a human or an animal, comprising:
a main body having a surface and a surrounding area;
at least one first material connected to the main body and including at least one cell proliferation-inhibiting first substance;
a second material that decomposes in an implanted condition, said second material providing a covering layer over the first substance that prevents contact of the first substance with the surrounding area of the main body while in a first condition before beginning to decompose and that allows contact between the first substance and the surrounding area of the main body while in a second condition after beginning to decompose; and
a third material which is connected to the main body and which includes a cell proliferation-promoting second substance;
wherein the covering layer is sufficiently thick to maintain the first condition after implantation for a first time interval that is long enough for a body tissue coating to form and enclose at least a portion of the main body surface, and the first time interval is at least a week, and wherein the first material is present with respect to the surrounding area of the main body in a first deposit, which in the first condition is shielded by the covering layer, and wherein the third material promotes cell proliferation prior to expiry of the first time interval.

12. The implant of claim 11, wherein the first deposit is formed by a first layer connected to the main body and the covering is formed by a second layer covering the first layer.

13. The implant of claim 11, wherein the first deposit is arranged in a first recess of the main body, the covering being formed by a cover portion closing the first recess.

14. The implant of claim 13, wherein at least a portion of the main body surface is porous for forming a number of first recesses.

15. The implant of claim 11, wherein the first deposit is enclosed in a microcapsule which forms the covering and which is connected to the main body.

16. The implant of claim 11, wherein: the concentration and nature of the second substance are so selected that the cell proliferation-promoting action is substantially concluded prior to or with the expiry of the first time interval.

17. The implant of claim 11, wherein the main body comprises a stent.

18. The implant of claim 11, wherein the first time interval is at least two weeks.

19. The implant of claim 11, wherein the first time interval is less than four weeks.

20. The implant of claim 11, wherein the main body comprises a stent.

* * * * *